US009949624B2

(12) United States Patent
Igarashi

(10) Patent No.: US 9,949,624 B2
(45) Date of Patent: Apr. 24, 2018

(54) LIVING BODY OBSERVATION SYSTEM WITH CONTRAST ENHANCEMENT PROCESSING

(71) Applicant: OLYMPUS CORPORATION, Tokyo (JP)

(72) Inventor: Makoto Igarashi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/177,388

(22) Filed: Jun. 9, 2016

(65) Prior Publication Data

US 2016/0278621 A1 Sep. 29, 2016

Related U.S. Application Data

(63) Continuation of application No. PCT/JP2014/074083, filed on Sep. 11, 2014.

(30) Foreign Application Priority Data

Mar. 28, 2014 (JP) .................................. 2014-069674

(51) Int. Cl.
*A61B 1/06* (2006.01)
*A61B 1/04* (2006.01)
(Continued)

(52) U.S. Cl.
CPC .............. *A61B 1/0638* (2013.01); *A61B 1/00* (2013.01); *A61B 1/00006* (2013.01);
(Continued)

(58) Field of Classification Search
CPC ..... A61B 1/00009; A61B 1/043; A61B 1/045; A61B 1/05; A61B 1/06; A61B 1/0638;
(Continued)

(56) References Cited

U.S. PATENT DOCUMENTS

2005/0261551 A1\* 11/2005 Couvillon, Jr. .... A61B 1/00059
600/118
2009/0156901 A1 6/2009 Gono
(Continued)

FOREIGN PATENT DOCUMENTS

EP 1929930 A1 6/2008
EP 2641525 A1 9/2013
(Continued)

OTHER PUBLICATIONS

International Search Report dated Dec. 16, 2014 issued in PCT/JP2014/074083.
(Continued)

*Primary Examiner* — Anhtuan T Nguyen
*Assistant Examiner* — William Chou
(74) *Attorney, Agent, or Firm* — Scully, Scott, Murphy & Presser, P.C.

(57) ABSTRACT

A living body observation system includes: an illuminating light generation section configured to generate first light and second light; an image pickup section; a computation section configured to calculate a difference degree indicating a degree of difference between a luminance value of a first image obtained by picking up an image of return light of the first light and a luminance value of a second image obtained by picking up an image of return light of the second light in a same pixel; an enhancement processing section configured to enhance a contrast of the pixel in which the difference degree exceeds a threshold relative to a pixel in which the difference degree does not exceed the threshold; and an observation image creation section configured to create an observation image by using the first image after the process by the enhancement processing section and the second image.

1 Claim, 12 Drawing Sheets

(51) Int. Cl.
  *A61B 1/00* (2006.01)
  *G02B 23/26* (2006.01)
  *G02B 23/24* (2006.01)
  *A61B 1/05* (2006.01)
  *A61B 5/1455* (2006.01)
  *A61B 5/1459* (2006.01)

(52) U.S. Cl.
  CPC ...... *A61B 1/00009* (2013.01); *A61B 1/00045* (2013.01); *A61B 1/04* (2013.01); *A61B 1/05* (2013.01); *A61B 1/0676* (2013.01); *A61B 5/1459* (2013.01); *A61B 5/14551* (2013.01); *G02B 23/2484* (2013.01); *G02B 23/26* (2013.01)

(58) Field of Classification Search
  CPC ... A61B 1/0646; A61B 1/0653; A61B 1/0661; A61B 1/0669
  USPC ....... 600/109, 160, 178, 179, 180, 181, 182; 348/68, 69, 70; 382/128, 274
  See application file for complete search history.

(56) References Cited

U.S. PATENT DOCUMENTS

| | | |
|---|---|---|
| 2012/0179050 A1 | 7/2012 | Saito |
| 2013/0006109 A1 | 1/2013 | Takei et al. |
| 2013/0030268 A1* | 1/2013 | Saito .................. A61B 1/00009 600/325 |
| 2013/0176411 A1 | 7/2013 | Igarashi et al. |
| 2013/0289415 A1 | 10/2013 | Koshikawa |
| 2014/0081083 A1* | 3/2014 | Morita .................. A61B 1/0646 600/109 |
| 2014/0180129 A1 | 6/2014 | Kostenich et al. |

FOREIGN PATENT DOCUMENTS

| | | |
|---|---|---|
| EP | 2 687 145 A1 | 1/2014 |
| JP | 2007-097649 A | 4/2007 |
| JP | 2010-131265 A | 6/2010 |
| JP | 5220961 B2 | 6/2013 |
| JP | 5355820 B2 | 11/2013 |
| JP | 2014-504938 A | 2/2014 |
| WO | WO 2007/039981 A1 | 4/2007 |
| WO | WO 2012/098798 A1 | 7/2012 |
| WO | WO 2012/107884 A1 | 8/2012 |
| WO | 2014/014956 A1 | 1/2014 |

OTHER PUBLICATIONS

Japanese Office Action dated Oct. 27, 2015 issued in JP 2015-538791.

Extended Supplementary European Search Report dated Aug. 9, 2017 in European Patent Application No. 14 88 7381.3.

* cited by examiner

LIVING BODY OBSERVATION SYSTEM WITH CONTRAST ENHANCEMENT PROCESSING

CROSS REFERENCE TO RELATED APPLICATION

This application is a continuation application of PCT/JP2014/074083 filed on Sep. 11, 2014 and claims benefit of Japanese Application No. 2014-069674 filed in Japan on Mar. 28, 2014, the entire contents of which are incorporated herein by this reference.

BACKGROUND OF THE INVENTION

1. Field of the Invention

The present invention relates to a living body observation system, and particularly, to a living body observation system used for observation of living tissue.

2. Description of the Related Art

ESD (endoscopic submucosal dissection) has been proposed in recent years as an example of a method of treating a lesion site, such as cancer, under endoscopic observation. An endoscope system that can be utilized in ESD is disclosed in, for example, Japanese Patent No. 5355820.

More specifically, an endoscope system is disclosed in Japanese Patent No. 5355820, wherein based on an amount of enhancement set for a region with a distribution of an observation target in a subject (blood vessel of deep part under mucosal surface, pit pattern of mucosal epithelium, or blood vessel of mucosal epithelium) in a feature space formed based on wavelength bands or spatial frequency bands of two or more band images selected from a plurality of band images, an enhancement process is applied to the selected two or more band images, and a color conversion process of adjusting a tone is applied to the plurality of band images including the two or more band images after the enhancement process.

Furthermore, a method is used to treat a lesion site such as cancer, wherein a dye such as indigo carmine is administered to a submucosa of a region to be treated including the lesion site to thereby allow visually recognizing a layer boundary of the submucosa and a muscular layer.

SUMMARY OF THE INVENTION

An aspect of the present invention provides a living body observation system including: an illuminating light generation section configured to generate first light with a peak wavelength in a blue region and second light with a peak wavelength in a red region; an image pickup section configured to pick up an image of return light from an object illuminated by the light emitted from the illuminating light generation section; a computation section configured to calculate a difference degree that is a value indicating a degree of difference between a luminance value of a first image obtained by picking up an image of return light of the first light and a luminance value of a second image obtained by picking up an image of return light of the second light in a same pixel; an enhancement processing section configured to execute a process of increasing a luminance value of a pixel in which the difference degree exceeds a predetermined threshold among respective pixels included in the first image in order to enhance a contrast of the pixel in which the difference degree exceeds the predetermined threshold relative to a pixel in which the difference degree calculated by the computation section does not exceed the predetermined threshold; and an observation image creation section configured to create an observation image by using the first image after the process by the enhancement processing section and the second image and output the created observation image to a display apparatus.

An aspect of the present invention provides a living body observation system including: an illuminating light generation section configured to generate first light with a peak wavelength in a blue region and second light with a peak wavelength in a red region; an image pickup section configured to pick up an image of return light from an object illuminated by the light emitted from the illuminating light generation section; a computation section configured to calculate, for each pixel, an amount of variation that is a value indicating variation of a luminance value relative to an average value of luminance values of a second image based on the second image obtained by picking up an image of return light of the second light; an enhancement processing section configured to execute a process of increasing a luminance value of a pixel in which the amount of variation exceeds a predetermined threshold among respective pixels included in the first image in order to enhance a contrast of the pixel in which the amount of variation exceeds the predetermined threshold relative to a pixel in which the amount of variation calculated by the computation section does not exceed the predetermined threshold; and an observation image creation section configured to create an observation image by using the first image after the process by the enhancement processing section and the second image and output the created observation image to a display apparatus.

DETAILED DESCRIPTION OF THE PREFERRED EMBODIMENTS

Hereinafter, embodiments of the present invention will be described with reference to the drawings.

First Embodiment

Figure 1:
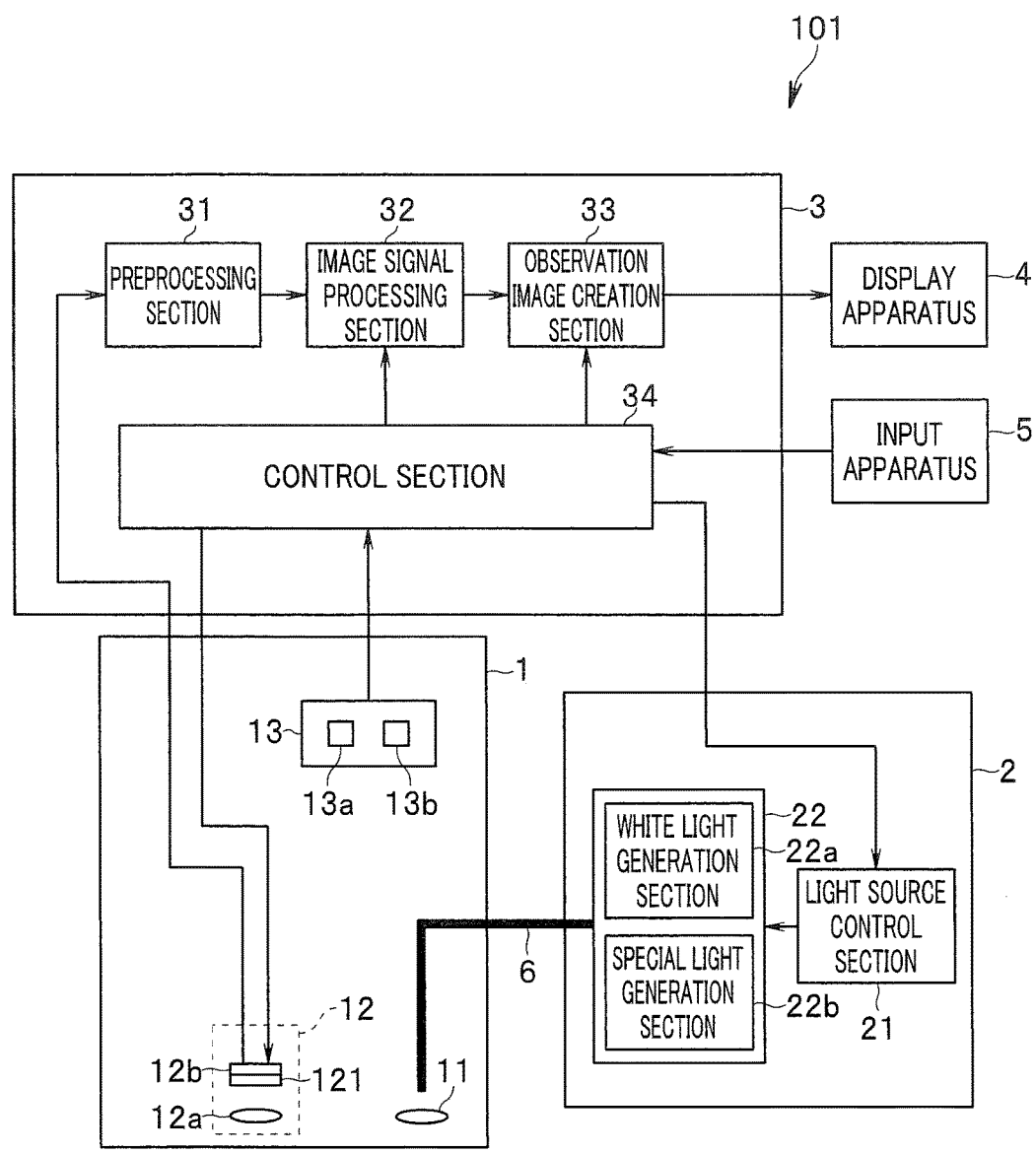
FIG. 1 is a diagram showing a configuration of main parts of a living body observation system according to an embodiment.

FIGS. 1 to 9 relate to a first embodiment of the present invention. FIG. 1 is a diagram showing a configuration of main parts of a living body observation system according to the embodiment.

As shown in FIG. 1, a living body observation system 101 is equipped with an insertion portion in an elongated shape that can be inserted into a subject that is a living body, and the living body observation system 101 includes: an endoscope 1 configured to pick up an image of an object, such as living tissue, in the subject and output an image pickup signal; a light source apparatus 2 configured to supply light used for observation of the object through a light guide 6 inserted and arranged inside of the endoscope 1; a processor 3 configured to create and output an observation image or the like according to the image pickup signal outputted from the endoscope 1; a display apparatus 4 configured to display the observation image or the like outputted from the processor 3; and an input apparatus 5 including a switch and/or a button capable of issuing an instruction or the like according to input operation by a user to the processor 3.

A distal end portion of the insertion portion of the endoscope 1 is provided with: an illumination optical system 11 configured to emit the light transmitted by the light guide 6 to the object; and an image pickup section 12 configured to output an image pickup signal obtained by picking up an image of reflected light (return light) emitted from the object according to the light emitted from the illumination optical system 11. The endoscope 1 also includes a scope switch 13 capable of issuing various instructions according to operation by the user to the processor 3.

The image pickup section 12 is configured to output the image pickup signal by picking up the image of the reflected light (return light) from the object illuminated by the illuminating light emitted from the light source apparatus 2. More specifically, the image pickup section 12 includes: an objective optical system 12a configured to form an image of the reflected light (return light) emitted from the object; and an image pickup device 12b in which an image pickup surface including a primary color filter 121 is arranged according to an image formation position of the objective optical system 12a.

The image pickup device 12b includes, for example, a CCD and is driven according to an image pickup device drive signal outputted from the processor 3. The image pickup device 12b is configured to output the image pickup signal obtained by picking up the image of the reflected light (return light) from the object formed on the image pickup surface.

The scope switch 13 includes an observation mode change-over switch 13a and an enhancement display change-over switch 13b.

The observation mode change-over switch 13a is configured to be able to instruct the processor 3 to set (switch) an observation mode of the living body observation system 101 to one of a white light observation mode and a special light observation mode according to operation by the user.

The enhancement display change-over switch 13b is configured to be able to instruct the processor 3 to set (switch) ON/OFF of a predetermined enhancement process (described later) in the special light observation mode according to operation by the user.

The light source apparatus 2 includes: a light source control section 21; and a light emitting unit 22 including a white light generation section 22a and a special light generation section 22b.

The light source control section 21 includes, for example, a control circuit. When, for example, the light source control section 21 detects that the observation mode of the living body observation system 101 is set to the white light observation mode based on a system control signal outputted from the processor 3, the light source control section 21 is configured to cause the white light generation section 22a to generate white light, create a light emission control signal for turning off the special light generation section 22b, and output the created light emission control signal to the light emitting unit 22.

When, for example, the light source control section 21 detects that the observation mode of the living body observation system 101 is set to the special light observation mode based on a system control signal outputted from the processor 3, the light source control section 21 is configured to turn off the white light generation section 22a, create a light emission control signal for sequentially generating NB1 light, NR1 light, and NR2 light described later from the special light generation section 22b, and output the created light emission control signal to the light emitting unit 22.

The white light generation section 22a includes, for example, one or more LEDs and is configured to be able to generate white light that is broadband light including a red region, a green region, and a blue region based on a light emission control signal outputted from the light source control section 21. Note that the white light generation section 22a of the present embodiment is not limited to those including one or more LEDs, and the white light generation section 22a may include, for example, a xenon lamp.

Figure 2:
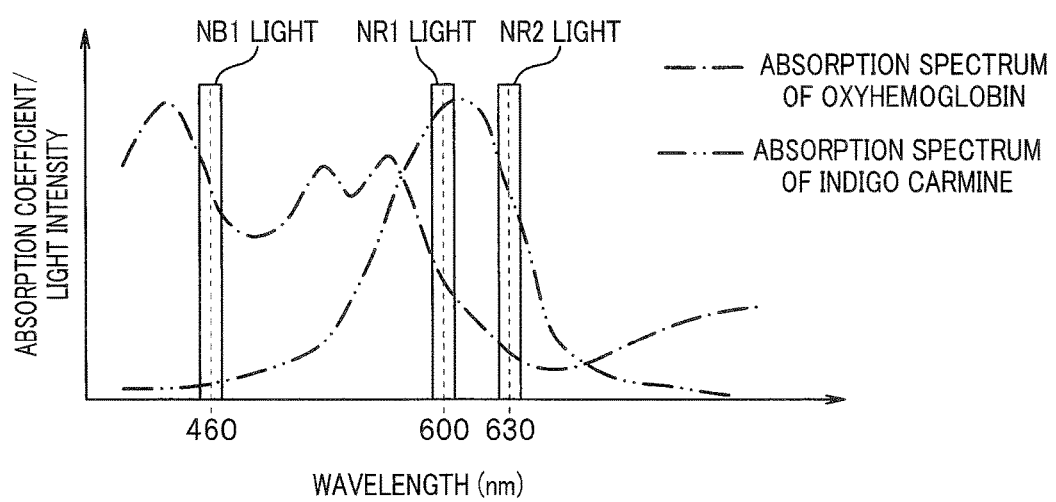
FIG. 2 is a diagram for describing an example of wavelengths of light emitted from a light source apparatus when an observation mode of the living body observation system is set to a special light observation mode according to the embodiment.

The special light generation section 22b includes, for example, a plurality of LEDs and is configured to be able to individually or simultaneously generate the NB1 light that is narrow-band blue light, the NR1 light that is narrow-band red light, and the NR2 light that is narrow-band red light set to a wavelength band different from the NR1 light based on a light emission control signal outputted from the light source control section 21. FIG. 2 is a diagram for describing an example of wavelengths of the light emitted from the light source apparatus when the observation mode of the living body observation system is set to the special light observation mode according to the embodiment.

As shown for example in FIG. 2, the NB1 light is blue light set to have a peak wavelength and a bandwidth such that an absorption coefficient of indigo carmine that is a dye with an absorption peak near 610 nm belonging to the red region is sufficiently smaller than an absorption coefficient of oxyhemoglobin. Note that in the present embodiment, the wavelength band of the NB1 light is preferably set to have a peak wavelength of 460 nm that is a wavelength indicating an absorption coefficient smaller than an absorption peak of oxyhemoglobin in the blue region.

As shown for example in FIG. 2, the NR1 light is red light set to have a peak wavelength of 600 nm that is a wavelength with the absorption coefficient of oxyhemoglobin in the red region greater than that of the NR2 light and set to have a bandwidth not overlapping the NR2 light.

As shown for example in FIG. 2, the NR2 light is red light set to have a peak wavelength of 630 nm that is a wavelength in which the absorption coefficient of oxyhemoglobin is sufficiently smaller than the absorption coefficient of indigo carmine, the absorption coefficient of oxyhemoglobin in the red region is smaller than that of the NR1 light, and the absorption coefficient of indigo carmine is greater than that of the NB1 light and set to have a bandwidth not overlapping the NR1 light.

The processor 3 includes a preprocessing section 31, an image signal processing section 32, an observation image creation section 33, and a control section 34.

The preprocessing section 31 includes, for example, a noise reduction circuit and an A/D conversion circuit and is configured to create a digital image signal by applying a process, such as noise removal and A/D conversion, to the image pickup signal outputted from the endoscope 1 and output the created image signal to the image signal processing section 32.

The image signal processing section 32 includes, for example, a signal processing circuit. When, for example, the image signal processing section 32 detects that the observation mode of the living body observation system 101 is set to the white light observation mode based on a system control signal outputted from the control section 34, the image signal processing section 32 is configured to isolate the image signal outputted from the preprocessing section 31 into respective color components of R (red) components, G (green) components, and B (blue) components obtained by picking up an image of the reflected light (return light) of the white light and output the color components to the observation image creation section 33.

When, for example, the image signal processing section 32 detects that the observation mode of the living body observation system 101 is set to the special light observation mode and that the predetermined enhancement process is set to OFF based on a system control signal outputted from the control section 34, the image signal processing section 32 is configured to isolate the image signal outputted from the preprocessing section 31 into respective color components of NB1 components obtained by picking up an image of the reflected light (return light) of the NB1 light, NR1 components obtained by picking up an image of the reflected light (return light) of the NR1 light, and NR2 components obtained by picking up an image of the reflected light (return light) of the NR2 light and output the color components to the observation image creation section 33.

When, for example, the image signal processing section 32 detects that the observation mode of the living body observation system 101 is set to the special light observation mode and that the predetermined enhancement process is set to ON based on a system control signal outputted from the control section 34, the image signal processing section 32 is configured to isolate the image signal outputted from the preprocessing section 31 into respective color components of the NB1 components, the NR1 components, and the NR2 components and apply the predetermined enhancement process based on each of the isolated color components to the NB1 components to output the components to the observation image creation section 33.

The observation image creation section 33 includes, for example, an image processing circuit. When, for example, the observation image creation section 33 detects that the observation mode of the living body observation system 101 is set to the white light observation mode based on a system control signal outputted from the control section 34, the observation image creation section 33 is configured to allocate luminance values of the R components outputted from the image signal processing section 32 to an R channel corresponding to red of the display apparatus 4, allocate luminance values of the G components outputted from the image signal processing section 32 to a G channel corresponding to green of the display apparatus 4, and allocate luminance values of B components outputted from the image signal processing section 32 to a B channel corresponding to blue of the display apparatus 4 to create an observation image. The observation image creation section 33 is configured to output the created observation image to the display apparatus 4.

When, for example, the observation mode of the living body observation system 101 is set to the special light observation mode based on a system control signal outputted from the control section 34, the observation image creation section 33 is configured to allocate luminance values of the NR2 components outputted from the image signal processing section 32 to the R channel, allocate luminance values of the NR1 components outputted from the image signal processing section 32 to the G channel, and allocate luminance values of the NB1 components outputted from the image signal processing section 32 to the B channel to create an observation image. The observation image creation section 33 is configured to output the created observation image to the display apparatus 4.

The control section 34 is configured to create and output an image pickup device drive signal for driving the image pickup device 12b.

The control section 34 includes, for example, a CPU or a control circuit and is configured to create a system control signal for performing operation corresponding to the observation mode set in the observation mode change-over switch 13a and output the system control signal to the light source control section 21, the image signal processing section 32, and the observation image creation section 33.

The control section 34 is configured to create a system control signal for performing operation corresponding to ON/OFF of the predetermined enhancement process set in the enhancement display change-over switch 13b and output the system control signal to the image signal processing section 32.

Next, action of the living body observation system according to the present embodiment will be described. Note that specific operation when the observation mode of the living body observation system 101 is set to the white light observation mode will not be described below for the simplification.

The user turns on a power source of each section of the living body observation system 101 and sets the observation mode of the living body observation system 101 to the white light observation mode. The user then inserts the insertion portion of the endoscope 1 into the subject while checking the observation image (white light image) displayed on the display apparatus 4.

The user arranges the distal end portion of the insertion portion of the endoscope 1 near a region to be treated including a lesion site, such as cancer, in the subject and administers (local injection or spraying) indigo carmine (dye) to a submucosa of the region to be treated. The user then operates the observation mode change-over switch 13a to set the observation mode of the living body observation system 101 to the special light observation mode and operates the enhancement display change-over switch 13b to set the predetermined enhancement process to ON.

When the control section 34 detects that the observation mode of the living body observation system 101 is set to the special light observation mode, the control section 34 creates, for example, a system control signal that can specify each of timing for simultaneously generating the NB1 light and the NR2 light and timing for independently generating the NR1 light and outputs the system control signal to the light source control section 21, the image signal processing section 32, and the observation image creation section 33.

Based on a system control signal outputted from the control section 34, the light source control section 21 sequentially and repeatedly controls the special light generation section 22b to simultaneously generate the NB1 light and the NR2 light and independently generate the NR1 light. The NB1 light, the NR1 light, and the NR2 light that are illuminating light for illuminating the object are sequentially emitted through the illumination optical system 11 according to the control by the light source control section 21. An image pickup signal obtained by picking up an image of the reflected light (return light) from the object is outputted from the image pickup device 12b, and an image signal created based on the image pickup signal from the image pickup device 12b is outputted from the preprocessing section 31.

Note that according to the present embodiment, when, for example, a monochrome image pickup device not including the primary color filter 121 is provided on the image pickup section 12 in place of the image pickup device 12b including the primary color filter 121, control for independently generating the NB1 light, control for independently generating the NR1 light, and control for independently generating the NR2 light may be sequentially repeated.

The image signal processing section 32 isolates the image signal outputted from the preprocessing section 31 into respective color components of the NB1 components, the NR1 components, and the NR2 components and applies the predetermined enhancement process to the isolated NB1 components.

Figure 3:
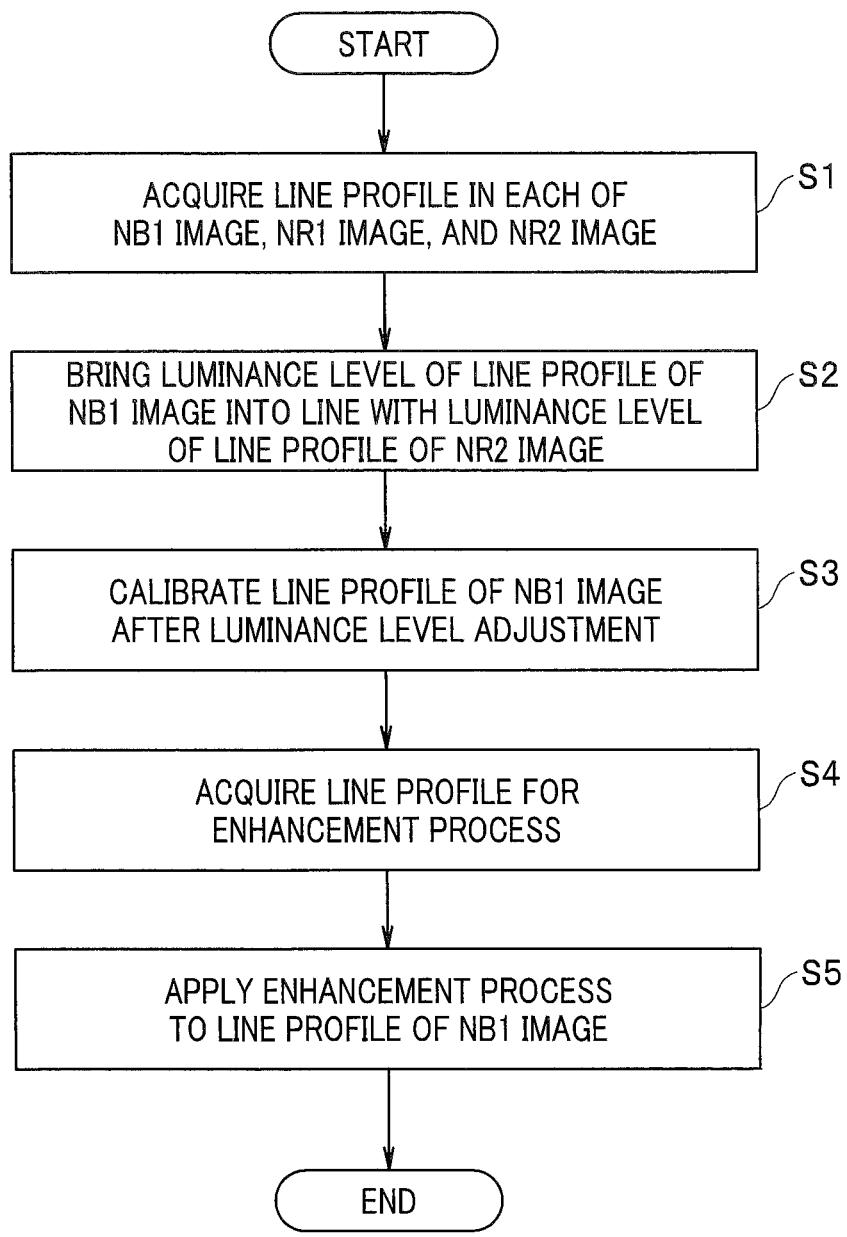
FIG. 3 is a flowchart for describing an enhancement process according to a first embodiment.

Here, details of the enhancement process executed by the image signal processing section 32 of the present embodiment will be described by appropriately referring to a flowchart of FIG. 3. FIG. 3 is a flowchart for describing the enhancement process according to the first embodiment.

Figure 4:
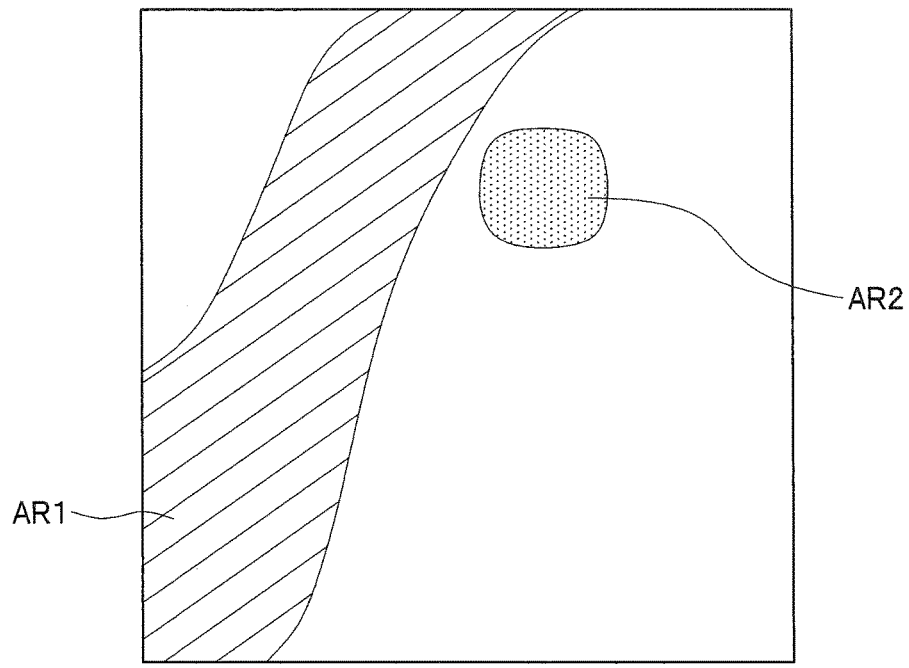
FIG. 4 is a diagram showing an example of an image to be processed in the enhancement process according to the first embodiment.

Note that an example of applying the enhancement process to an image signal obtained by picking up an image of the object including a region AR1 provided with indigo carmine and a region AR2 with bleeding (small amount) associated with damage or the like of a blood vessel as shown in FIG. 4 will be described below for the simplification. In the following description, the enhancement process is executed based on an NB1 image, an NR1 image, and an NR2 image corresponding to the respective color components obtained by isolating the image signal from the preprocessing section 31 for the simplification. FIG. 4 is a diagram showing an example of an image to be processed in the enhancement process according to the first embodiment.

Figure 5:
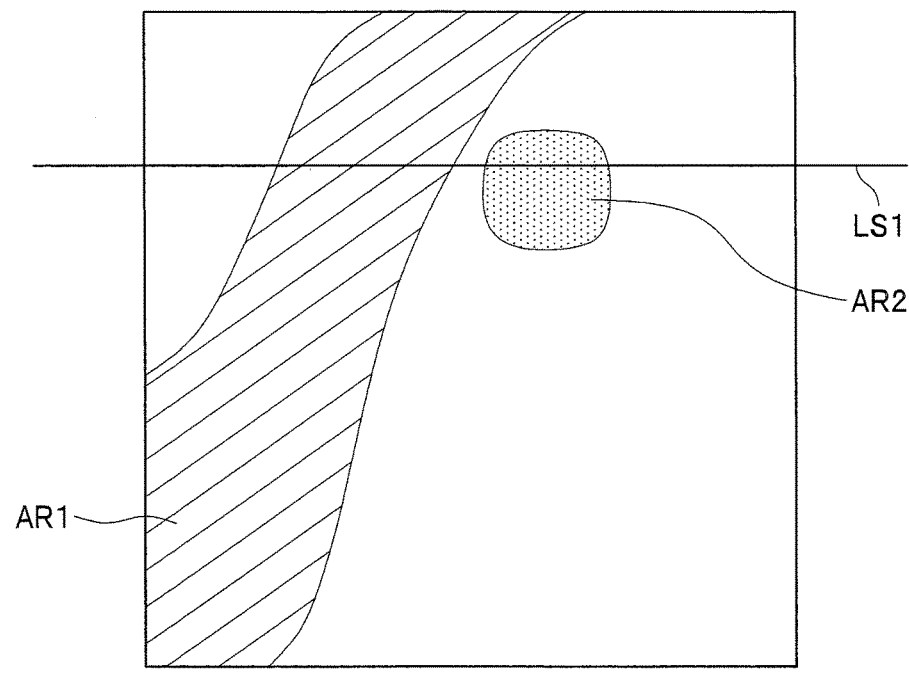
FIG. 5 is a diagram showing a line segment LS1 used to acquire line profiles from the image of FIG. 4.
Figure 6:
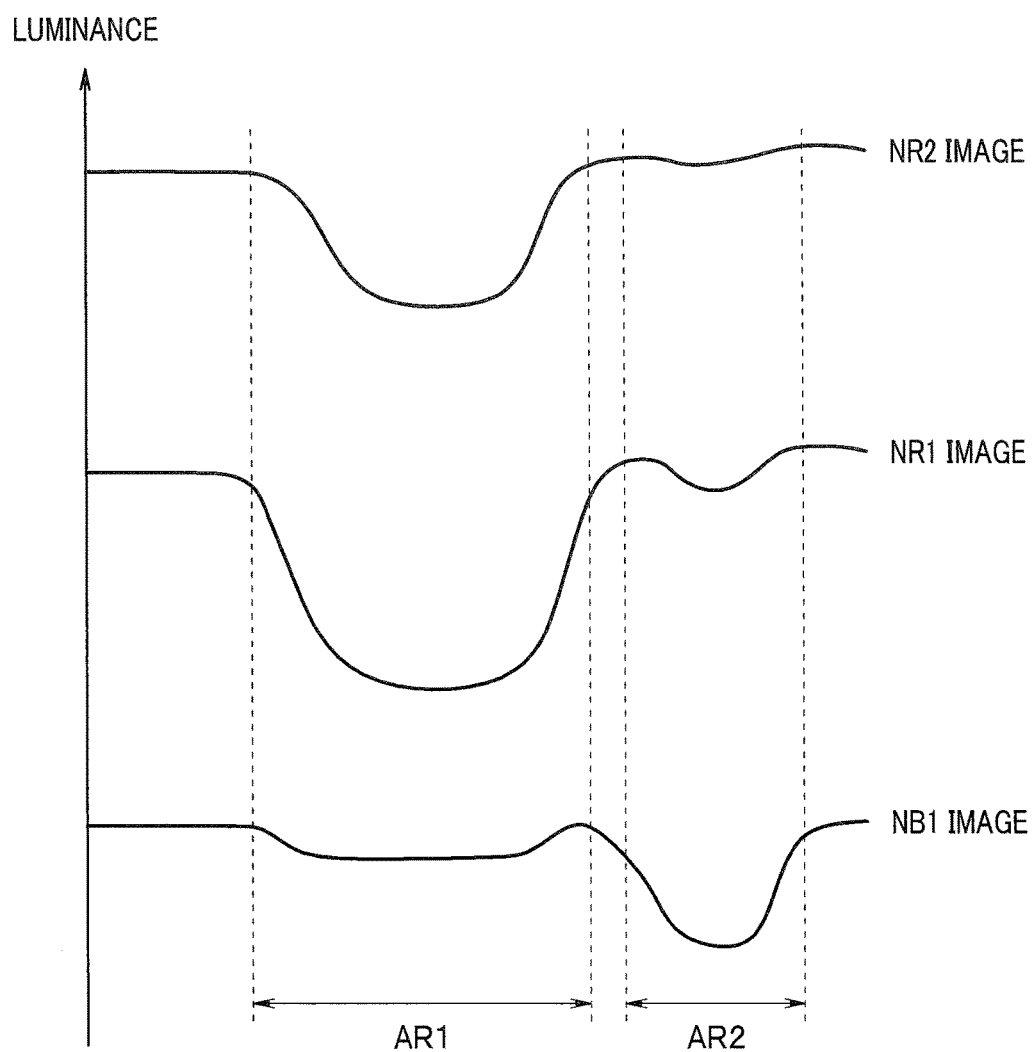
FIG. 6 is a diagram showing an example of the line profiles acquired from respective pixels positioned on the line segment LS1 of FIG. 5.

The image signal processing section 32 executes a process of acquiring line profiles (luminance information) indicating a distribution state of luminance values of respective pixels positioned on line segments parallel to a horizontal direction of the image in each of the NB1 image, the NR1 image, and the NR2 image, wherein the number of line profiles is equivalent to the number of pixels in a perpendicular direction of the image (step S1 of FIG. 3). In an example described below, line profiles as shown in FIG. 6 are acquired in the process as information indicating the distribution state of the luminance values of the respective pixels positioned on a line segment LS1 shown in FIG. 5 in the image shown in FIG. 4, for the simplification. FIG. 5 is a diagram showing the line segment LS1 used to acquire the line profiles from the image of FIG. 4. FIG. 6 is a diagram showing an example of the line profiles acquired from the respective pixels positioned on the line segment LS1 of FIG. 5. Note that in FIG. 6, a magnitude relationship of luminance values between the respective images of the NB1 image, the NR1 image, and the NR2 image is not accurately illustrated for the simplification of the illustration.

The image signal processing section 32 executes a computation process of bringing a luminance level of a line profile LP1 of the NB1 image acquired in the process of step S1 of FIG. 3 into line with a luminance level of a line profile LP2 of the NR2 image acquired in the process of step S1 of FIG. 3 (step S2 of FIG. 3).

More specifically, the image signal processing section 32 executes, for example, a process of calculating an average value AV1 of the luminance values of the respective pixels included in a predetermined region (for example, entire image) in the NB1 image and an average value AV2 of the luminance values of the respective pixels included in the predetermined region in the NR2 image and further multiplying the respective luminance values included in the line profile LP1 by a value (AV2/AV1) obtained by dividing the average value AV2 by the average value AV1 in step S2 of FIG. 3.

The image signal processing section 32 executes a process of using the line profile LP2 to calibrate a line profile LB1 of the NB1 image after the luminance level adjustment obtained as a processing result of step S2 of FIG. 3 (set a reference value of the luminance values in the line profile LB1 to 0) (step S3 of FIG. 3).

Figure 7:
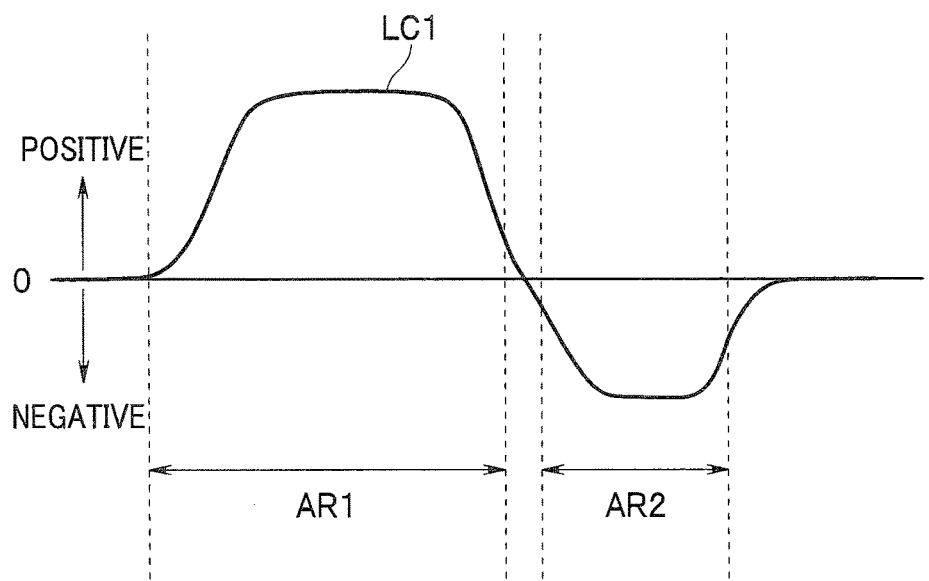
FIG. 7 is a diagram showing an example of a line profile LC1 acquired in the enhancement process according to the first embodiment.

More specifically, the image signal processing section 32 executes, for example, a process of dividing the luminance value of one pixel included in the line profile LB1 by the luminance value of the one pixel included in the line profile LP2 and further executes a computation process of subtracting 1 from each luminance value obtained in the process in step S3 of FIG. 3. When the computation process is executed in step S3 of FIG. 3, a line profile LC1 of the NB1 image is acquired (see FIG. 7), in which the luminance values of the pixels in the region AR1 are indicated by values greater than 0, and the luminance values of the pixels in the region AR2 are indicated by values equal to or smaller than 0. FIG. 7 is a diagram showing an example of the line profile LC1 acquired in the enhancement process according to the first embodiment.

Note that the image signal processing section 32 of the present embodiment is not limited to those configured to execute the process described above to acquire the line profile LC1 in step S3 of FIG. 3. For example, the image signal processing section 32 may execute a process of subtracting the luminance value of one pixel included in the line profile LP2 from the luminance value of the one pixel included in the line profile LB1 to acquire the line profile LC1.

That is, the image signal processing section 32 that functions as a computation section executes a process of calculating, as the line profile LC1, a difference degree that is a value indicating a degree of difference between the luminance values of the NB1 image and the NR2 image in the same pixel in step S2 and step S3 of FIG. 3.

On the other hand, when, for example, a maximum luminance value MBL in the NB1 image is smaller than a maximum luminance value MRL in the NR2 image, and a difference value between the maximum luminance value MRL and the maximum luminance value MBL is small, the image signal processing section 32 of the present embodiment may skip the process of step S2 of FIG. 3 and execute a process described below in step S3 of FIG. 3 to acquire the line profile LC1.

More specifically, for example, the image signal processing section 32 may skip the process of step S2 of FIG. 3 in the case described above. Then, the image signal processing section 32 may execute a process of dividing the luminance value of one pixel included in the line profile LP1 by the luminance value of the one pixel included in the line profile LP2 and execute a computation process of subtracting 1 from each luminance value obtained in the process to acquire the line profile LC1 in step S3 of FIG. 3.

Alternatively, for example, the image signal processing section 32 may skip the process of step S2 of FIG. 3 in the case described above. Then, the image signal processing section 32 may execute a process of subtracting the luminance value of one pixel included in the line profile LP2 from the luminance value of the one pixel included in the line profile LP1 and execute a computation process of subtracting 1 from each luminance value obtained in the process to acquire the line profile LC1 in step S3 of FIG. 3.

Based on the line profile LC1 of the NB1 image obtained as a processing result of step S3 of FIG. 3, the image signal processing section 32 executes a process of acquiring a line profile LE1 for enhancement process including enhancement coefficients of respective pixels positioned on the line segment LS1 (step S4 of FIG. 3).

Figure 8:
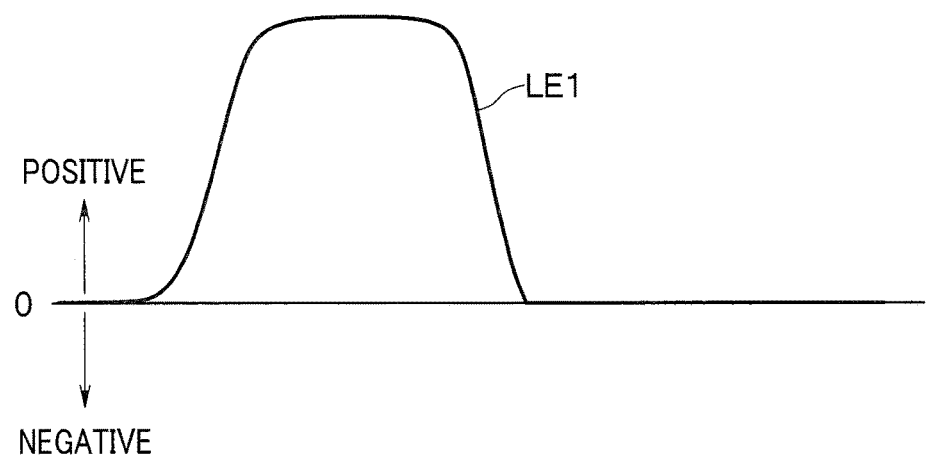
FIG. 8 is a diagram showing an example of a line profile LE1 acquired in the enhancement process according to the first embodiment.

More specifically, for example, the image signal processing section 32 executes a process of maintaining the luminance values greater than 0 in the line profile LC1 and evenly converting the luminance values equal to or smaller than 0 into 0 and then executes a process of multiplying the respective luminance values obtained in the process by a constant RA (RA>1) to thereby calculate the enhancement coefficients of the respective pixels positioned on the line segment LS1 in step S4 of FIG. 3. When such a process is executed in step S4 of FIG. 3, the line profile LE1 for enhancement process as illustrated in FIG. 8 is acquired. FIG. 8 is a diagram showing an example of the line profile LE1 acquired in the enhancement process according to the first embodiment.

In other words, the image signal processing section 32 that functions as an enhancement coefficient calculation section executes a process of calculating the enhancement coefficients of the respective pixels positioned on the line segment LS1 based on the line profile LC1 to acquire the respective calculated enhancement coefficients as the line profile LE1 in step S4 of FIG. 3. In other words, the image signal processing section 32 executes a process of calculating the enhancement coefficients for increasing the luminance values of the pixels in the region AR1 and maintaining the luminance values of the pixels outside of the region AR1 among the respective pixels positioned on the line segment LS1 based on the line profile LC1 in step S4 of FIG. 3. In other words, the image signal processing section 32 executes a process of calculating the enhancement coefficients corresponding to the pixels in which the difference degrees calculated in the processes of step S2 and step S3 of FIG. 3 exceed a predetermined threshold in step S4 of FIG. 3.

The image signal processing section 32 that functions as an enhancement processing section applies an enhancement process of maintaining a contrast of the region AR2 and enhancing a contrast of the region AR1 to the line profile LP1 based on the respective enhancement coefficients included in the line profile LE1 for enhancement process obtained as a processing result of step S4 of FIG. 3 (step S5 of FIG. 3).

More specifically, for example, the image signal processing section 32 applies a process of adding a luminance value La of one pixel in the line profile LP1 and a value (Ea×La) obtained by multiplying an enhancement coefficient Ea corresponding to the one pixel in the line profile LE1 by the luminance value La (La+Ea×La) to each pixel included in the line profile LP1 in step S5 of FIG. 3.

That is, in step S5 of FIG. 3, the image signal processing section 32 executes a process of enhancing contrasts of the pixels in which the difference degree calculated in the process of step S2 and step S3 of FIG. 3 exceeds the predetermined threshold among the respective pixels included in the NB1 image based on the enhancement coefficients calculated in the process of step S4 of FIG. 3.

The image signal processing section 32 outputs, to the observation image creation section 33, the NB1 image created by executing the enhancement process (for each line profile) as shown in FIG. 3 and the NR1 image and the NR2 image obtained by isolating the image signal outputted from the preprocessing section 31.

The observation image creation section 33 creates an observation image by allocating the luminance values of the NR2 image outputted from the image signal processing section 32 to the R channel, allocating the luminance values of the NR1 image outputted from the image signal processing section 32 to the G channel, and allocating the luminance values of the NB1 image outputted from the image signal processing section 32 in the state after the enhancement process to the B channel and outputs the created observation image to the display apparatus 4. According to the operation of the observation image creation section 33, an observation image is displayed on the display apparatus 4, in which an intensity of blue of the region AR1 is higher than when the enhancement process is not executed, and an intensity of red of the region AR2 is substantially the same as when the enhancement process is not executed, for example.

Figure 9:
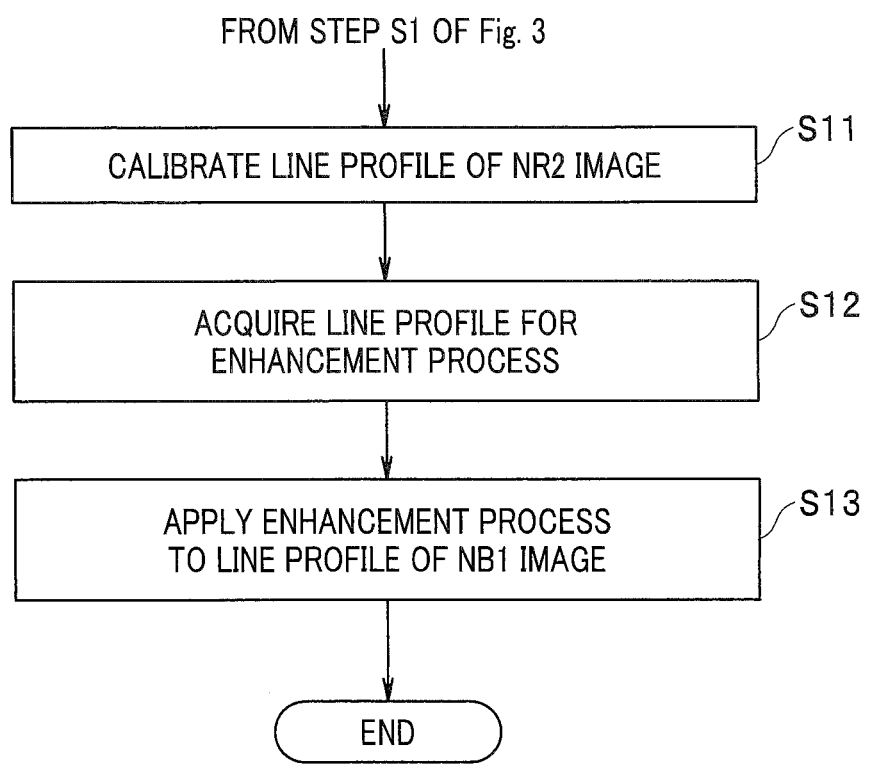
FIG. 9 is a flowchart for describing an enhancement process according to a modification of the first embodiment.

Note that the image signal processing section 32 of the present embodiment is not limited to those configured to execute the enhancement process as shown in FIG. 3, and for example, the image signal processing section 32 may execute an enhancement process as shown in FIG. 9. FIG. 9 is a flowchart for describing an enhancement process according to a modification of the first embodiment.

After the execution of the process of step S1 of FIG. 3, the image signal processing section 32 executes a process of calibrating the line profile LP2 of the NR2 image acquired in the process (setting the reference value of the luminance values in the line profile LP2 to 0) (step S11 of FIG. 9).

More specifically, for example, the image signal processing section 32 executes a computation process of calculating the average value AV2 of the luminance values of the respective pixels included in a predetermined region of the NR2 image and subtracting the average value AV2 from the respective luminance values included in the line profile LP2 in step S11 of FIG. 9.

That is, the image signal processing section 32 that functions as a computation section executes a process of calculating, for each pixel, an amount of variation that is a value indicating variation of the luminance value with respect to the average value of the luminance values of the NR2 image in step S11 of FIG. 9.

The image signal processing section 32 executes a process of acquiring a line profile LE2 for enhancement process including enhancement coefficients of the respective pixels positioned on the line segment LS1 based on a line profile LC2 of the NR2 image obtained as a processing result of step S11 of FIG. 9 (step S12 of FIG. 9).

More specifically, for example, the image signal processing section 32 executes a process of acquiring absolute values of the respective luminance values included in the line profile LC2, maintaining the luminance values greater than 0 in the acquired absolute values of the respective luminance values, and evenly converting the luminance values equal to or smaller than 0 into 0 and further executes a process of multiplying the respective luminance values obtained in the process by a constant RB (RB>1) to thereby calculate enhancement coefficients of the respective pixels positioned on the line segment LS1 in step S12 of FIG. 9.

In other words, the image signal processing section 32 that functions as an enhancement coefficient calculation section executes a process of calculating the enhancement coefficients of the respective pixels positioned on the line segment LS1 based on the line profile LC2 to acquire the respective calculated enhancement coefficients as the line profile LE2 in step S12 of FIG. 9. In other words, the image signal processing section 32 executes a process of calculating the enhancement coefficients for increasing the luminance values of the pixels in the region AR1 and maintaining the luminance values of the pixels outside of the region AR1 among the respective pixels positioned on the line segment LS1 based on the line profile LC2 in step S12 of FIG. 9. In other words, the image signal processing section 32 executes a process of calculating the enhancement coefficients corresponding to the pixels in which the amount of variation calculated in the process of step S11 of FIG. 9 exceeds the predetermined threshold in step S12 of FIG. 9.

The image signal processing section 32 that functions as an enhancement processing section applies an enhancement process of maintaining the contrast of the region AR2 and enhancing the contrast of the region AR1 to the line profile LP1 based on the respective enhancement coefficients included in the line profile LE2 for enhancement process obtained as a processing result of step S12 of FIG. 9 (step S13 of FIG. 9).

More specifically, for example, the image signal processing section 32 applies a process of adding a luminance value Lb of one pixel in the line profile LP1 and a value (Eb×Lb) obtained by multiplying an enhancement coefficient Eb corresponding to the one pixel in the line profile LE2 by the luminance value Lb (Lb+Eb×Lb) to each pixel included in the line profile LP1 in step S13 of FIG. 9.

That is, in step S13 of FIG. 9, the image signal processing section 32 executes a process of enhancing the contrasts of the pixels in which the amount of variation calculated in the process of step S11 of FIG. 9 exceeds the predetermined threshold among the respective pixels included in the NB1 image based on the enhancement coefficients calculated in the process of step S12 of FIG. 9.

The image signal processing section 32 outputs, to the observation image creation section 33, the NB1 image created by executing the enhancement process (for each line profile) as shown in FIG. 9 and the NR1 image and the NR2 image obtained by isolating the image signal outputted from the preprocessing section 31.

The observation image creation section 33 creates an observation image by allocating the luminance values of the NR2 image outputted from the image signal processing section 32 to the R channel, allocating the luminance values of the NR1 image outputted from the image signal processing section 32 to the G channel, and allocating the luminance values of the NB1 image outputted from the image signal processing section 32 in the state after the enhancement process to the B channel and outputs the created observation image to the display apparatus 4. According to the operation of the observation image creation section 33, an observation image is displayed on the display apparatus 4, in which the intensity of blue of the region AR1 is higher than when the enhancement process is not executed, and the intensity of red of the region AR2 is substantially the same as when the enhancement process is not executed, for example.

As described, according to the present embodiment, the observation image after the enhancement process of maintaining the contrast of the region AR2 (without affecting the contrast of the region AR2) and enhancing the contrast of the region AR1 can be displayed on the display apparatus 4. According to the present embodiment, even when a concentration of indigo carmine in the region AR1 is low for example, an observation image that allows visually recognizing the region AR1 can be displayed on the display apparatus 4. Therefore, according to the present embodiment, visibility of a layer boundary of a submucosa and a muscular layer can be improved without deteriorating visibility of a bleeding site associated with damage or the like of a blood vessel. That is, a load of an operator in treating a lesion site, such as cancer, can be reduced.

Note that the special light generation section 22b of the present embodiment may be configured to generate, for example, NB2 light that is narrow-band blue light with a peak wavelength of 415 nm, in place of the NB1 light.

When the observation mode of the living body observation system 101 is set to the special light observation mode, the observation image creation section 33 of the present embodiment may be configured to create the observation image by allocating the luminance values of the NR1 image outputted from the image signal processing section 32 to the R channel and the G channel and allocating the luminance values of the NB1 image outputted from the image signal processing section 32 in the state after the enhancement process to the B channel, for example.

On the other hand, according to the present embodiment, the process of calculating the enhancement coefficients is not limited to those executed for each line profile, and for example, the process may be executed for each pixel. The process may be executed for each region of interest including a plurality of pixels or may be collectively executed for all pixels in the image.

Second Embodiment

FIGS. 10 to 16 relate to a second embodiment of the present invention.

Note that in the present embodiment, parts with the same components and the like as in the first embodiment are not described in detail, and parts with components and the like different from the first embodiment will be mainly described.

A living body observation system of the present embodiment includes substantially the same components as the respective sections of the living body observation system 101 described in the first embodiment. On the other hand, the image signal processing section 32 is configured to execute an enhancement process different from the first embodiment.

When the image signal processing section 32 of the present embodiment detects that the observation mode of the living body observation system 101 is set to the special light observation mode and that the predetermined enhancement process is set to ON based on a system control signal outputted from the control section 34, the image signal processing section 32 is configured to isolate the image signal outputted from the preprocessing section 31 into respective color components of the NB1 components, the NR1 components, and the NR2 components and apply the predetermined enhancement process based on the respective isolated color components to the NB1 components and the NR1 components to output the components to the observation image creation section 33.

Figure 10:
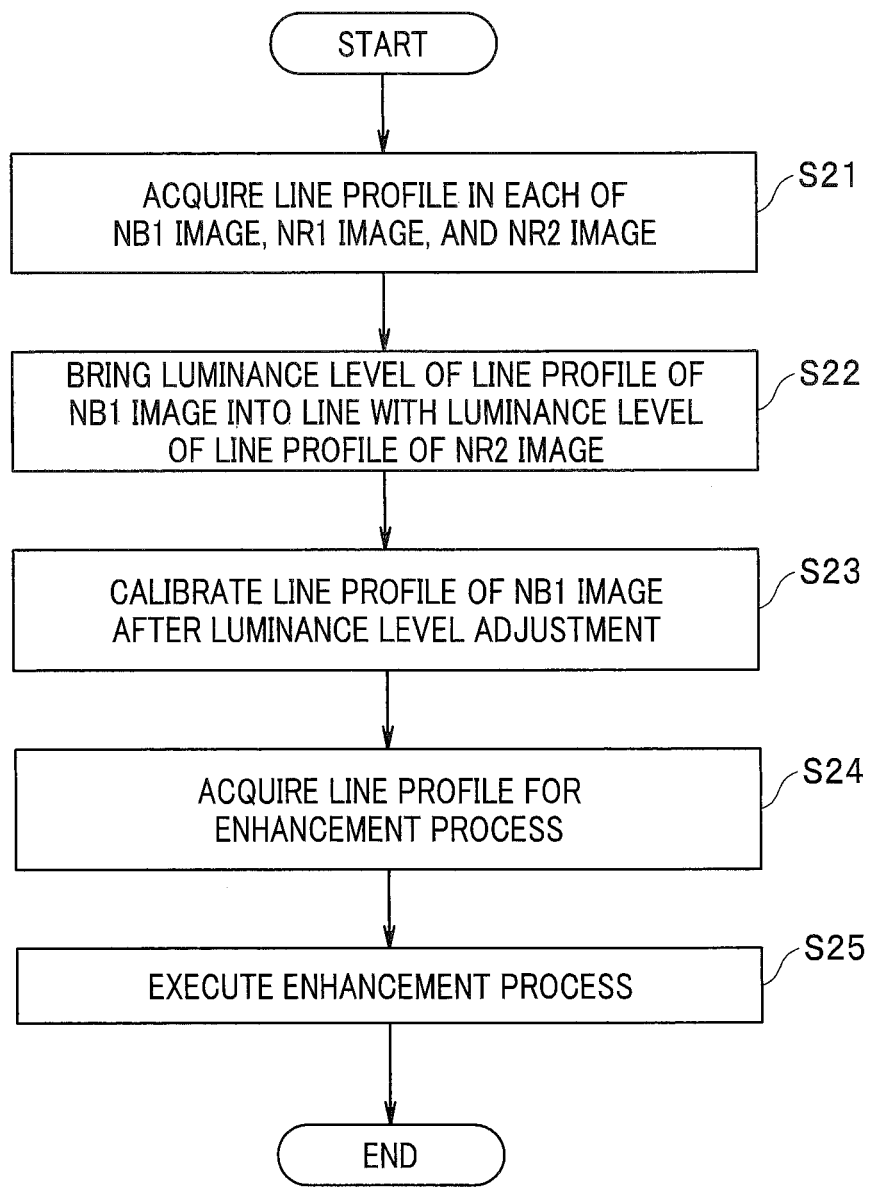
FIG. 10 is a flowchart for describing an enhancement process according to a second embodiment.

Next, details of the enhancement process executed by the image signal processing section 32 of the present embodiment will be described by appropriately referring to a flowchart of FIG. 10. FIG. 10 is a flowchart for describing the enhancement process according to the second embodiment.

Figure 11:
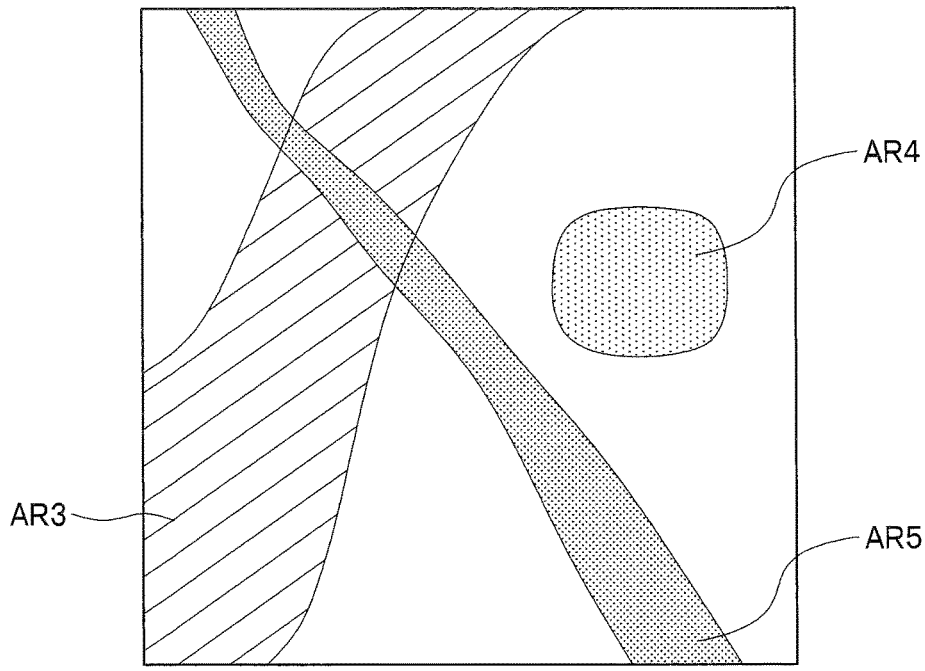
FIG. 11 is a diagram showing an example of an image to be processed in the enhancement process according to the second embodiment.

Note that in an example described below, the enhancement process is applied to an image signal obtained by picking up an image of an object including a region AR3 provided with indigo carmine, a region AR4 with bleeding (small amount) associated with damage or the like of a blood vessel, and a region AR5 including a deep blood vessel (blood vessel with large diameter) running through a submucosa as shown in FIG. 11, for the simplification. In the following description, the enhancement process is executed based on the NB1 image, the NR1 image, and the NR2 image corresponding to the respective color components obtained by isolating the image signal from the preprocessing section 31, for the simplification. FIG. 11 is a diagram showing an example of an image to be processed in the enhancement process according to the second embodiment.

Figure 12:
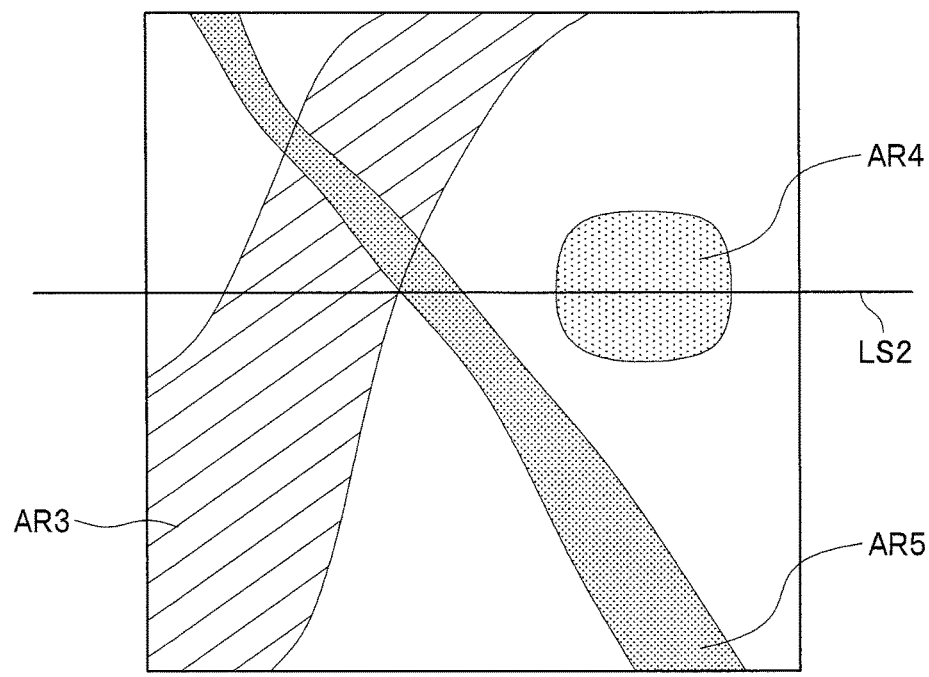
FIG. 12 is a diagram showing a line segment LS2 used to acquire line profiles from the image of FIG. 11.
Figure 13:
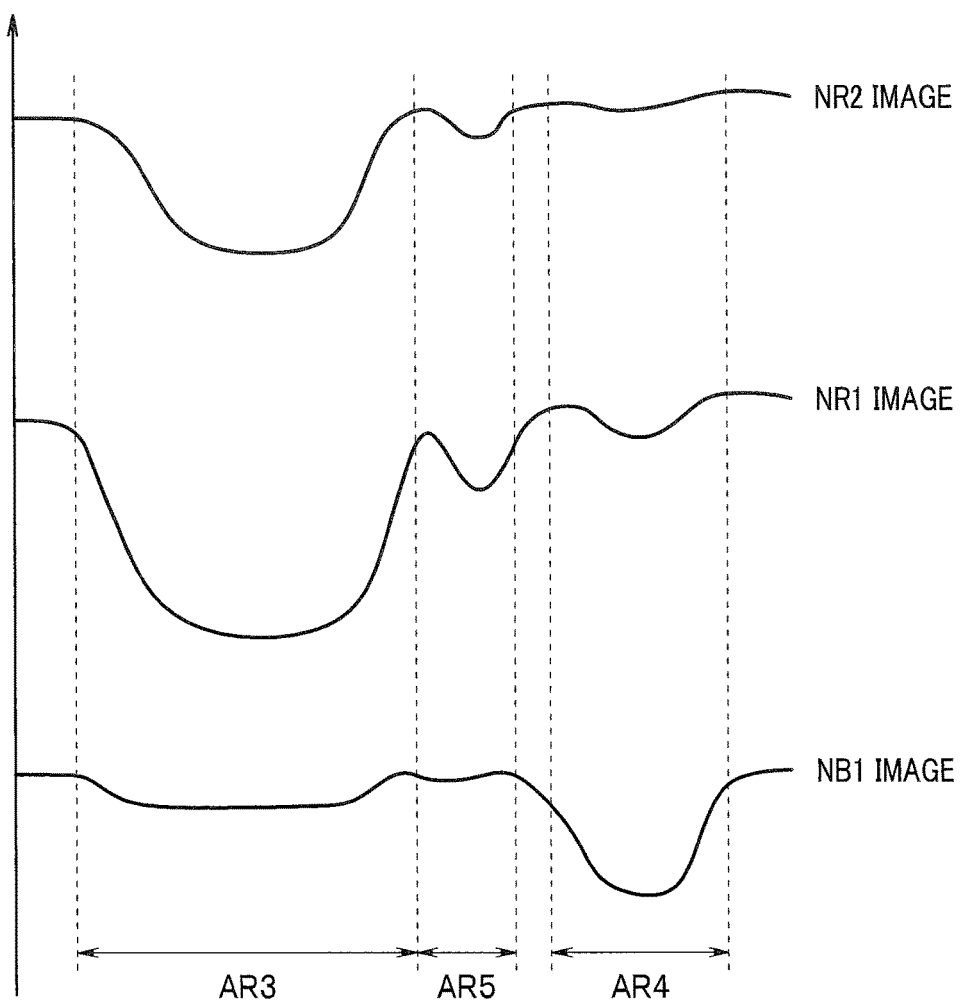
FIG. 13 is a diagram showing an example of the line profiles acquired from respective pixels positioned on the line segment LS2 of FIG. 12.

The image signal processing section 32 executes a process of acquiring line profiles that are information indicating a distribution state of luminance values of respective pixels positioned on line segments parallel to the horizontal direction of the image in each of the NB1 image, the NR1 image, and the NR2 image, wherein the number of line profiles is equivalent to the number of pixels in the perpendicular direction of the image (step S21 of FIG. 10). In an example described below, line profiles as shown in FIG. 13 are acquired as the information indicating the distribution state of the luminance values of the respective pixels positioned on a line segment LS2 shown in FIG. 12 as a result of the process described above, for the simplification. FIG. 12 is a diagram showing the line segment LS2 used to acquire the line profiles from the image of FIG. 11. FIG. 13 is a diagram showing an example of the line profiles acquired from the respective pixels positioned on the line segment LS2 of FIG. 12. Note that in FIG. 13, a magnitude relationship of luminance values between the respective images of the NB1 image, the NR1 image, and the NR2 image is not accurately illustrated for the simplification of the illustration.

The image signal processing section 32 executes a computation process of bringing a luminance level of a line profile LP3 of the NB1 image acquired in the process of step S21 of FIG. 10 into line with a luminance level of a line profile LP4 of the NR2 image acquired in the process of step S21 of FIG. 10 (step S22 of FIG. 10).

More specifically, the image signal processing section 32 executes, for example, a process of calculating an average value AV3 of the luminance values of the respective pixels included in a predetermined region (for example, entire image) in the NB1 image and an average value AV4 of the luminance values of the respective pixels included in the predetermined region in the NR2 image and further multiplying the respective luminance values included in the line profile LP3 by a value (AV4/AV3) obtained by dividing the average value AV4 by the average value AV3 in step S22 of FIG. 10.

The image signal processing section 32 executes a process of using the line profile LP4 to calibrate a line profile LB2 of the NB1 image after the luminance level adjustment obtained as a processing result of step S22 of FIG. 10 (set a reference value of the luminance values in the line profile LB2 to 0) (step S23 of FIG. 10).

Figure 14:
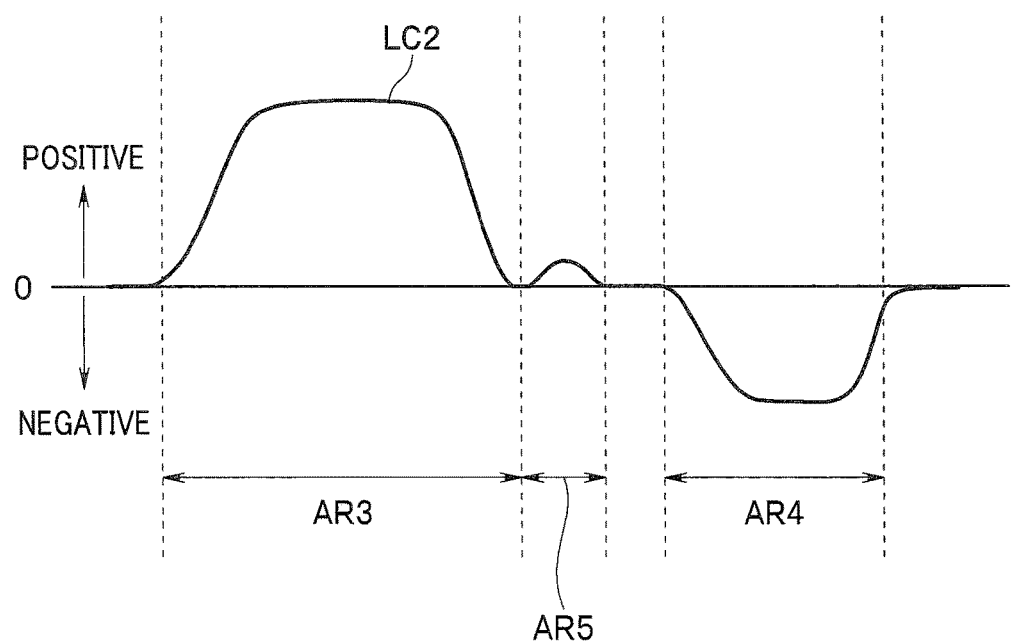
FIG. 14 is a diagram showing an example of a line profile LC2 acquired in the enhancement process according to the second embodiment.

More specifically, the image signal processing section 32 executes, for example, a process of dividing the luminance value of one pixel included in the line profile LB2 by the luminance value of the one pixel included in the line profile LP4 and further executes a computation process of subtracting 1 from each luminance value obtained in the process in step S23 of FIG. 10. When the computation process is executed in step S23 of FIG. 10, the line profile LC2 of the NB1 image is acquired (see FIG. 14), in which the luminance values of the pixels in the region AR3 and the region AR5 are indicated by values greater than 0, and the luminance values of the pixels in the region AR4 are indicated by values equal to or smaller than 0. FIG. 14 is a diagram showing an example of the line profile LC2 acquired in the enhancement process according to the second embodiment.

That is, the image signal processing section 32 that functions as a computation section executes a process of calculating, as the line profile LC2, a difference degree that is a value indicating a degree of difference between the luminance values of the same pixel in the NB1 image and the NR2 image in step S22 and step S23 of FIG. 10.

Based on the line profile LC2 of the NB1 image obtained as a processing result of step S23 of FIG. 10, the image signal processing section 32 executes a process of acquiring line profiles LE3 and LE4 for enhancement process including enhancement coefficients of respective pixels positioned on the line segment LS2 (step S24 of FIG. 10).

Figure 15:
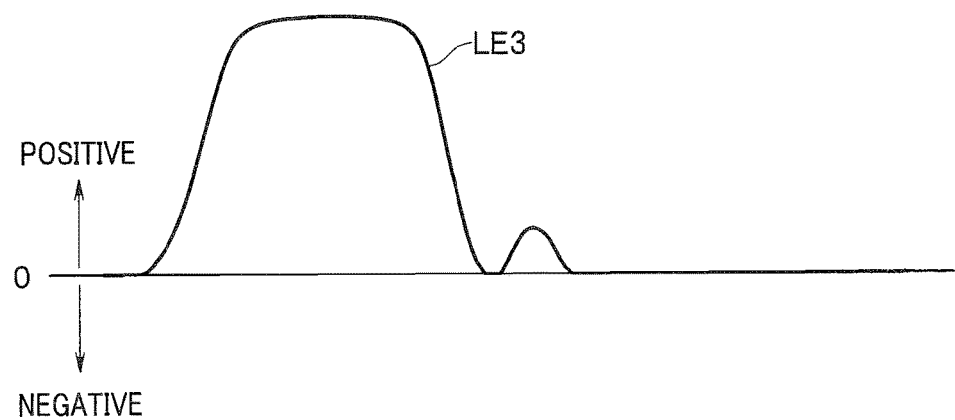
FIG. 15 is a diagram showing an example of a line profile LE3 acquired in the enhancement process according to the second embodiment.
Figure 16:
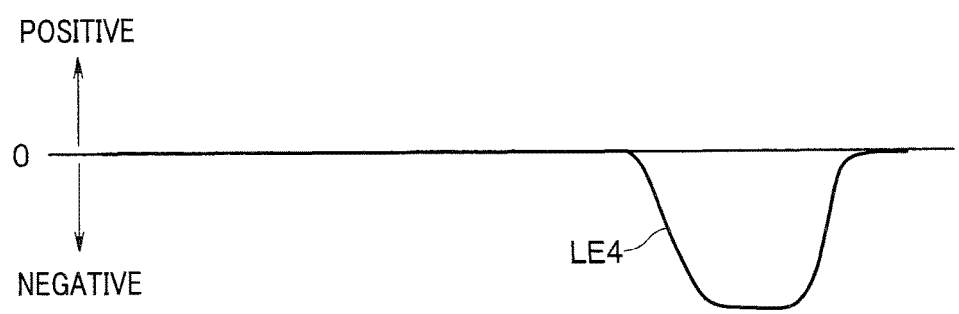
FIG. 16 is a diagram showing an example of a line profile LE4 acquired in the enhancement process according to the second embodiment.

More specifically, for example, the image signal processing section 32 executes a process of maintaining the luminance values greater than 0 in the line profile LC2 and evenly converting the luminance values equal to or smaller than 0 into 0 and further executes a process of multiplying the respective luminance values obtained in the process by a constant RC (RC>1) to thereby calculate the enhancement coefficients of the respective pixels positioned on the line segment LS2 in step S24 of FIG. 10. When such a process is executed in step S24 of FIG. 10, the line profile LE3 for enhancement process as illustrated in FIG. 15 is acquired. Furthermore, the image signal processing section 32 executes, for example, a process of maintaining the luminance values equal to or smaller than 0 in the line profile LC2 and evenly converting the luminance values greater than 0 into 0 and further executes a process of multiplying the respective luminance values obtained in the process by a constant RD (RD>1) to thereby calculate the enhancement coefficients of the respective pixels positioned on the line segment LS2 in step S24 of FIG. 10. When such a process is executed in step S24 of FIG. 10, the line profile LE4 for enhancement process as illustrated in FIG. 16 is acquired. FIG. 15 is a diagram showing an example of the line profile LE3 acquired in the enhancement process according to the second embodiment. FIG. 16 is a diagram showing an example of the line profile LE4 acquired in the enhancement process according to the second embodiment.

In other words, the image signal processing section 32 that functions as an enhancement coefficient calculation section executes a process of calculating the enhancement coefficients of the respective pixels positioned on the line segment LS2 based on the line profile LC2 to acquire the respective calculated enhancement coefficients as the line profile LE3 and the line profile LE4 in step S24 of FIG. 10. In other words, the image signal processing section 32 executes a process of calculating a first enhancement coefficient and a second enhancement coefficient based on the line profile LC2 in step S24 of FIG. 10, wherein the first enhancement coefficient is for increasing the luminance values of the pixels in the region AR3 and the luminance values of the pixels in the region AR5 among the respective pixels positioned on the line segment LS2 and maintaining the luminance values of the pixels outside of the region AR3 and outside of the region AR5, and the second enhancement coefficient is for reducing the luminance values of the pixels in the region AR4 and maintaining the luminance values of the pixels outside of the region AR4. In other words, the image signal processing section 32 executes a process of calculating the enhancement coefficients corresponding to the pixels in which the difference degrees calculated in the processes of step S22 and step S23 of FIG. 10 exceed a predetermined threshold in step S24 of FIG. 10.

The image signal processing section 32 that functions as an enhancement processing section applies an enhancement process of maintaining a contrast of the region AR5 and enhancing contrasts of the region AR3 and the region AR4 to the line profile LP3 and a line profile LP5 of the NR1 image acquired in the process of step S21 of FIG. 10 based on the respective enhancement coefficients included in the line profiles LE3 and LE4 for enhancement process obtained as a processing result of step S24 of FIG. 10 (step S25 of FIG. 10).

More specifically, for example, the image signal processing section 32 applies a process of adding a luminance value Lc of one pixel included in the line profile LP3 and a value (Ec×Lc) obtained by multiplying an enhancement coefficient Ec corresponding to the one pixel in the line profile LE3 by the luminance value Lc (Lc+Ec×Lc) to each pixel included in the line profile LP3 in step S25 of FIG. 10. Furthermore, for example, the image signal processing section 32 applies a process of adding a luminance value Ld of one pixel included in the line profile LP5 and a value (Ed×Ld) obtained by multiplying an enhancement coefficient Ed corresponding to the one pixel in the line profile LE4 by the luminance value Ld (Ld+Ed×Ld) to each pixel included in the line profile LP5 in step S25 of FIG. 10.

That is, in step S25 of FIG. 10, the image signal processing section 32 executes a process of enhancing the contrasts of the pixels in which the difference degree calculated in the process of step S22 and step S23 of FIG. 10 exceeds the predetermined threshold among the pixels included in the NB1 image and the NR1 image based on the enhancement coefficients calculated in the process of step S24 of FIG. 10.

The image signal processing section 32 outputs the NB1 image created by executing the enhancement process (for each line profile) as shown in FIG. 10, the NR1 image created by executing the enhancement process (for each line profile) as shown in FIG. 10, and the NR2 image obtained by isolating the image signal outputted from the preprocessing section 31 to the observation image creation section 33.

The observation image creation section 33 creates an observation image by allocating the luminance values of the NR2 image outputted from the image signal processing section 32 to the R channel, allocating the luminance values of the NR1 image outputted from the image signal processing section 32 in the state after the enhancement process to the G channel, and allocating the luminance values of the NB1 image outputted from the image signal processing section 32 in the state after the enhancement process to the B channel and outputs the created observation image to the display apparatus 4.

According to the operation of the observation image creation section 33, an observation image is displayed on the display apparatus 4, in which the intensity of blue of the region AR3 is higher than when the enhancement process is not executed, the intensity of red of the region AR4 is higher than when the enhancement process is not executed, and the intensity of red of the region AR5 is substantially the same as when the enhancement process is not executed, for example.

Note that according to the present embodiment, a process of further increasing the intensity of red of the region AR4 may be included in the enhancement process of FIG. 10.

More specifically, for example, a process of applying a process of acquiring the line profile LE5 equivalent to the absolute values of the respective luminance values included in the line profile LE4 shown in FIG. 16 and adding a luminance value Le of one pixel included in the line profile LP4 and a value (Ee×Le) obtained by multiplying an enhancement coefficient Ee corresponding to the one pixel in the line profile LE5 by the luminance value Le (Le+Ee×Le) to each pixel included in the line profile L4 may be included in the enhancement process of FIG. 10. The luminance values of the NR2 image created through the process are allocated to the R channel, the luminance values of the NR1 image created through the enhancement process of FIG. 10 are allocated to the G channel, and the luminance values of the NB1 image created through the enhancement process of FIG. 10 are allocated to the B channel. As a result, an observation image can be displayed on the display apparatus 4, in which the intensity of blue of the region AR3 is higher than when the enhancement process is not executed, the intensity of red of the region AR4 is further increased compared to when the enhancement process of FIG. 10 is executed, and the intensity of red of the region AR5 is substantially the same as when the enhancement process is not executed.

According to the present embodiment, for example, the value of the constant RD in the enhancement process of FIG. 10 may be set to a sufficiently large value to further increase the intensity of red of the region AR4.

According to the present embodiment, for example, a process of enhancing the contrast of one of the region AR3 and the region AR4 may be executed in step S25 of FIG. 10.

As described, according to the present embodiment, the observation image after the enhancement process of maintaining the contrast of the region AR5 (without affecting the contrast of the region AR5) and increasing the contrasts of the region AR3 and the region AR4 can be displayed on the display apparatus 4. According to the present embodiment, even when the concentration of indigo carmine in the region AR3 is low for example, an observation image that allows visually recognizing the region AR3 can be displayed on the display apparatus 4. Therefore, according to the present embodiment, visibility of a layer boundary of a submucosa and a muscular layer as well as visibility of a bleeding site caused by damage or the like of a blood vessel can be improved without deteriorating visibility of a deep blood vessel (blood vessel with large diameter) running through the submucosa. That is, the load of the operator in treating a lesion site, such as cancer, can be reduced.

The present invention is not limited to each of the embodiments described above, and it is obvious that various changes and applications can be made without departing from the scope of the invention.

What is claimed is:

1. A living body observation system comprising:

an illuminating light generation section configured to generate first light with a peak wavelength in a blue region, second light with a peak wavelength in a red region, and third light, which is narrow-band red light, with a peak wavelength in which an absorption coefficient of oxyhemoglobin in the red region is greater than in the second light, the third light having a bandwidth not overlapping a bandwidth of the second light;

an image pickup section configured to pick up an image of return light from an object illuminated by the light emitted from the illuminating light generation section; and one or more processors comprising hardware, wherein the one or more processors are configured to:

receive a first image obtained by picking up an image of return light of the first light and having luminance values for a plurality of respective pixels and a second image obtained by picking up an image of return light of the second light and having luminance values for a plurality of respective pixels and, to calculate, for each pixel, a difference degree that is a value indicating a degree of difference between a luminance value in a pixel in the first image and a luminance value in a pixel in the second image, the pixel in the second image corresponding to the pixel in the first image;

identify, among the plurality of pixels, a pixel in which the difference degree exceeds a predetermined threshold and a pixel in which the difference degree does not exceed the predetermined threshold, based on the difference degree calculated for each pixel;

execute a first image process of enhancing a luminance value of the pixel in which the difference degree exceeds the predetermined threshold relative to luminance values of other pixels among the plurality of pixels constituting the first image and execute a second image process of enhancing a luminance value of a pixel in which the difference degree is equal to or smaller than the predetermined threshold to luminance values of other pixels among a plurality of pixels constituting a third image obtained by picking up an image of return light of the third light; and generate an observation image by allocating the luminance values of the plurality of pixels in the first image subjected to the first image process, the luminance values of the plurality of pixels in the second image, and the luminance values of the plurality of pixels in the third image subjected to the second image process to different color channels, and output the generated observation image to a display apparatus.

* * * * *